United States Patent [19]

Srivastava et al.

[11] Patent Number: 5,981,266

[45] Date of Patent: *Nov. 9, 1999

[54] MICROBIAL PROCESS FOR THE MITIGATION OF SULFUR COMPOUNDS FROM NATURAL GAS

[75] Inventors: Kailash C. Srivastava, Centreville; Daman S. Walia, Clifton, both of Va.

[73] Assignee: Gas Research Institute, Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/651,793

[22] Filed: May 20, 1996

[51] Int. Cl.$^6$ .................................. A61L 9/01; C12N 1/00
[52] U.S. Cl. ........................... 435/266; 435/262; 435/822
[58] Field of Search .................................. 435/266, 262, 435/822

[56] References Cited

U.S. PATENT DOCUMENTS

| | | | |
|---|---|---|---|
| 1,701,825 | 2/1929 | Seil | 435/266 |
| 4,242,448 | 12/1980 | Brown, III | 435/42 |
| 4,666,852 | 5/1987 | Cork | 435/262 |
| 4,758,417 | 7/1988 | van Lookerren-Campagne et al. | 423/231 |
| 4,760,027 | 7/1988 | Sublette | 435/266 |
| 4,880,542 | 11/1989 | Sublette | 210/611 |
| 4,931,262 | 6/1990 | Sonta et al. | 423/220 |
| 4,968,622 | 11/1990 | Berzaczy et al. | 435/266 |
| 4,971,151 | 11/1990 | Sheehy | 166/246 |
| 5,044,435 | 9/1991 | Sperl et al. | 166/246 |
| 5,077,208 | 12/1991 | Sublette | 435/168 |
| 5,217,615 | 6/1993 | Tyagi et al. | 210/611 |
| 5,232,676 | 8/1993 | Wolff et al. | 423/210 |
| 5,236,677 | 8/1993 | Torres-Cardona et al. | 423/230 |
| 5,250,102 | 10/1993 | Barnes et al. | 75/710 |
| 5,297,625 | 3/1994 | Premuzic et al. | 166/246 |
| 5,354,545 | 10/1994 | Buisman | 423/242.1 |
| 5,385,842 | 1/1995 | Weimer et al. | 435/262 |

FOREIGN PATENT DOCUMENTS

| | | |
|---|---|---|
| 0218958A2 | 4/1987 | European Pat. Off. |
| 0244659A2 | 11/1987 | European Pat. Off. |

OTHER PUBLICATIONS

Aerobic Oxidation of Hydrogen Sulfide by Thiobacillus Denitrificans, K. Sublette, Biotechnology and Bioengineering, vol. XXIX, pp. 690–695, (1987).
Biological Removal of $H_2S$ From Sour Natural Gas, K. Srivastava, Oct. 1992 GRI Liquid Redox Sulfur Recovery Conference, pp. 129, 131–145.
Optimization of Sulp[hur Production in a Biotechnological Sulphide–Removing Reactor, Buisman, et al., Biotechnology and Bioengineering, vol. 35, pp. 50–56, (1990).
Microbial Control of the Production of Hydrogen Sulfide by Sulfate–Reducing Bacteria, Montgomery et al., Biotechnology and Bioengineering, vol. 35, pp. 533–539, (1990).
Microbial Desulfurization of Gases, Sublette et al., Biotechnology and Bioengineering Symp. No. 17 (1986), pp. 543–564.
Microbial Reduction of Sulfur Dioxide with Pretreated Sewage Sludge and Elemental Hydrogen as Electron Donors, Deshmane, et al., Applied Biochemistry and Biotechnology, vol. 39/40, (1993), pp. 739–752.
Microbial Removal of Sulfur Dioxide from a Gas Stream with Net Oxidation to Sulfate, Dasu et al., Applied Biochemistry and Biotechnology, vol. 20/21, (1989), pp. 207–220.
Oxidation of Hydrogen Sulfide by Flocculated Thiobaccillus Dentrificans in a Continuous Culture, Biotechnology and Bioengineering, vol. 37, (1991) pp. 497–504.
Oxidation of Hydrogen Sulfide by Mixed Cultures of Thiobacillus Dentrificans and Heterotrophs, Sublette et al., Biotechnology and Bioengineering, vol. XXIX, (1987) 759–761.
Oxidation of Hydrogen Sulfide by Thiobacilli, Cadenhead et al., Biotechnology and Bioengineering, vol. 35, (1990) pp. 1150–1154.
Oxidation of Hydrogen Sulfide by Thiobacillus Dentrificans: Desulfurization of Natural Gas, Biotechnology and Bioengineering, vol. XXIX, (1987) pp. 249–257.
Production of Microbial Biomass Protein from Autotrophic Fermentation of Hydrogen Sulfide, Sublette, Biotechnology and Bioengineering, vol. 32, (1988) pp. 408–409.
Reduction of Sulfur Dioxide by Desulfovibrio Desulfuricans in Co–culture with Fermentative Heterotrophs, Dasu et al., Biotechnology and Bioengineering, vol. 34, (1989) pp. 405–409.
Removal Kinetics of Hydrogen Sulfide, Methanethiol and Dimethyl Sulfide by Peat Biofilters, Hirai et al., Journal of Fermentation and Bioengineering, vol. 70, No. 5, (1990) 334–339.
Immobilization of an Autotrophic Bacterium by Coculture with Floc–Forming Heterotrophs, Ongcharit, et al., Biotechnology and Bioengineering, vol. 33, (1989), pp. 1077–1080.
Immobilization of Thiobacillus Denitrificans for the Oxidation of Hydrogen Sulfide in Sour Water, Applied Biochemistry and Biotechnology, vol. 20/21 (1989) pp. 675–686.
Kinetics of Chemical and Biological Sulfide Oxidation in Aqueous Solutions, Buisman, et al. (1990). *(not included).
Biotechnological Process for Sulfide Removal with Sulfur Reclamation, Buisman, et al., ACTA Biotechnology, vol. 9, pp. 255–267, (1990). *(not included).

*Primary Examiner*—Leon B. Lankford, Jr.
*Assistant Examiner*—Christopher R. Tate
*Attorney, Agent, or Firm*—Pauley Petersen Kinne & Fejer

[57] ABSTRACT

An anaerobic process of desulfurizing a sour natural gas stream wherein a selected consortium of chemoautotrophic bacteria converts $H_2S$ and other sulfur species into elemental sulfur, which is recovered as a product. The process is conducted at pressures of up to 1000 psi and temperatures up to 140° F. (10° C. to 60° C.), and mitigates up to 10,000 ppm $H_2S$ to pipeline standards of $\leq 4$ ppm and up to 10% $CO_2$ to $\leq 2\%$ $CO_2$.

6 Claims, 9 Drawing Sheets

EXPERIMENTAL SET-UP FOR THE 2 L AND 14 L REACTORS

EXPERIMENTAL SET-UP FOR THE 1 L PARR PRESSURE REACTOR

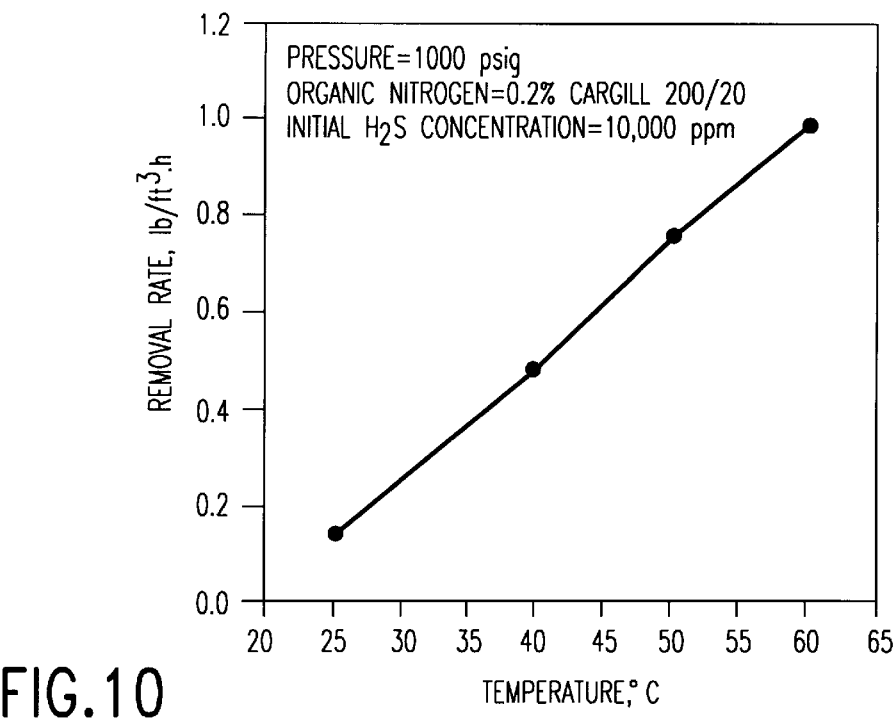
FIG.10 BIOCONVERSION OF $H_2S$ TO ELEMENTAL SULFUR IN PARR PRESSURE REACTOR AT DIFFERENT TEMPERATURES BY AMCC CONSORTIUM SSII
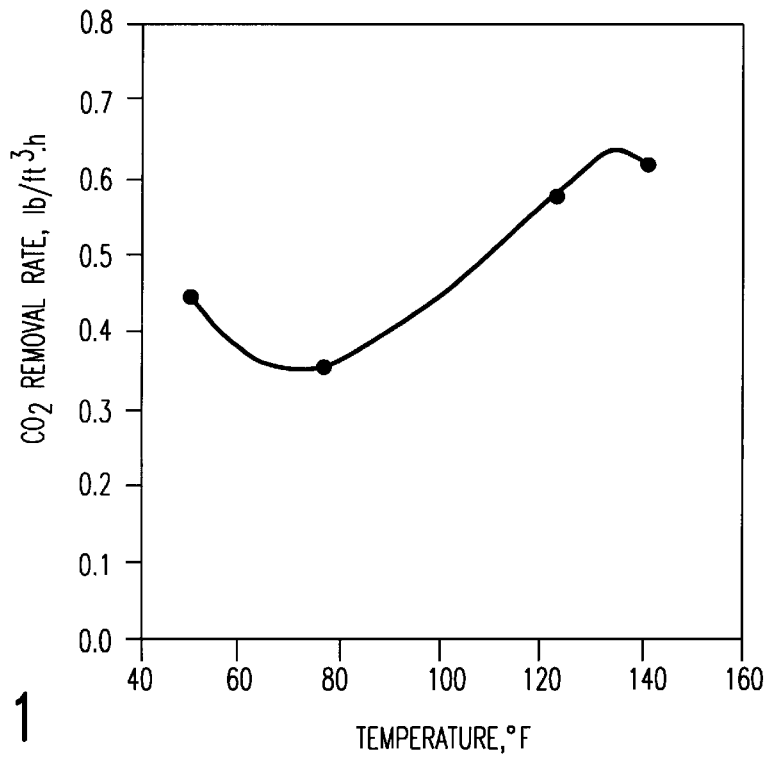
FIG.11 THE RATE OF REMOVAL OF $CO_2$ AT DIFFERENT TEMPERATURES IN 1-L PARR PRESSURE REACTOR WITH 10% SSII+0.2% CARGILL 200/20 AT 1000 psi

MICROBIAL PROCESS FOR THE MITIGATION OF SULFUR COMPOUNDS FROM NATURAL GAS

BACKGROUND OF THE INVENTION

The present invention relates to a process for removing $H_2S$ and other sulfur species under anaerobic conditions from sour gases. In particular, the present invention relates to the microbiological treatment of sour natural gas to remove $H_2S$ and other sulfur species, such as carbon disulfide, methyl mercaptan, ethyl mercaptan and dimethyl sulfide, from the natural gas stream, and recover elemental sulfur as a product of the process.

Natural gas reserves in the U.S. often contain hydrogen sulfide ($H_2S$) as a major contaminant. Hydrogen sulfide is an acid gas that is toxic and corrosive in the presence of water. A significant portion of total gas production does not meet pipeline standards and needs treatment to reduce the $H_2S$ concentration to ¼ grain per 100 standard cubic feet, or $\leq 4$ ppm on a volume basis.

A commonly used commercial process for the removal of $H_2S$ from the gas stream is the amine process, followed by the Claus process for sulfur recovery. In the amine process, the gas stream is contacted with the amine solvent to remove $H_2S$, then the amine solvent is heated to 90–150° C. (194–302° F.) to liberate $H_2S$ and regenerate the solvent, which is recycled. Although the $H_2S$ is removed from the natural gas stream, it still must be disposed of. Hydrogen sulfide generated during regeneration of the amine solvent can either be incinerated, which converts the hydrogen sulfide disposal problem into an air pollution problem due to the production of $SO_2$, or treated by physicochemical methods such as the Claus process. In the Claus process, $H_2S$ is fed into a reaction furnace, and the reaction gas is passed through a series of catalytic reactors to convert the $H_2S$ into elemental sulfur. Although the Claus process produces a high quality elemental sulfur product, the process is often too expensive for small capacity plants (of less than 2 MM SCFd).

Several microbiological methods have been investigated for the treatment of gas streams containing sulfides. In one process, the anaerobic photosynthetic bacterium *Chlorobium thiosulfatophilum* is used to convert sulfides to sulfate. Cork, D. J. and Ma, S. "Acid-Gas Bioconversion Favors Sulfur Production", Biotech. and Bioeng. Symp. No. 12, 285–290 (1982).

In another process, which is the basis for a process known as Bio-SR, the $Fe^{+2}$ formed during $H_2S$ oxidation in accordance with Equation (1), is converted to $Fe^{+3}$ by the bacterium *Thiobacillus ferroxidans* in accordance with Equation (2).

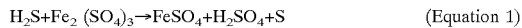  (Equation 1)

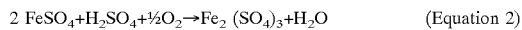  (Equation 2)

A number of bacteria (called chemoautotrophic) use reduced sulfur compounds as a source of energy, $CO_2$ or bicarbonate as a source of carbon, and $NH_4^+$ as a source of reduced nitrogen. *Thiobacillus denitrificans* is one such organism. One process for the desulfurization of gas using *Thiobacillus denitrificans* is disclosed in Sublette, U.S. Pat. No. 4,760,027. That patent describes a process wherein bacteria of the *Thiobacillus* genus convert sulfides to sulfates under aerobic conditions and at a controlled temperature of about 30° C.

Most of the studies on $H_2S$ removal have been performed under aerobic conditions and at $H_2S$ concentrations of <1000 ppm. Such methods, however, cannot be used for the direct removal of $H_2S$ from sour natural gas because of the potential danger of explosion when methane and air are mixed.

The process of the present invention overcomes these limitations and problems of prior art $H_2S$ removal processes because the process is carried out under anaerobic conditions. The process is known to be effective for treatment of inlet $H_2S$ concentrations of up to 10,000 ppm (1%), at a pressure of 1,000 psi and at temperatures common to those required by the gas industry (e.g. 140° F., 60° C.). In addition, the process of the present invention reduces $CO_2$ levels of from 5% to 10% down to 2%.

In earlier research, ARCTECH developed a microbial consortium, SSII, from ARCTECH'S Microbial Culture collection (AMCC) to reduce the $H_2S$ concentrations of up to 10,000 ppm to pipeline specifications of $\leq 4$ ppm. The biological and physiological characteristics of this consortium and technical feasibility of the consortium to mitigate 1% $H_2S$ to $\leq 4$ ppm are the subject of a separate patent application. The information from laboratory scale bioreactor experiments using SSII served as the basis for further research, which is the subject of the present invention. The preliminary data from the laboratory scale bioreactor experiments was presented at the 1992 GRI Liquid Redox Sulfur Recovery Conference, Austin, Tex. on Oct. 4–6, 1992, by K. C. Srivastava, and entitled "Biological Removal of $H_2S$ From Sour Natural Gas", which paper is hereby incorporated by reference in its entirety. The results from this preliminary work provided the experimental proof of the concept of biological $H_2S$ removal under anaerobic conditions on bench scale. Nevertheless, additional scaled-up processing information was necessary for delineating the process parameters.

SUMMARY OF THE INVENTION

An object of the present invention is to provide a method of desulfurizing sour natural gas by microbiological techniques under anaerobic conditions, and recovering elemental sulfur as a product.

Another object of the present invention is to mitigate $H_2S$, other sulfur species, namely methyl mercaptan, ethyl mercaptan, dimethyl sulfide, and carbon disulfide, as well as carbon dioxide, in sour natural gas.

A further object of the present invention is to provide a low cost, economical and efficient process for the removal of $H_2S$ from natural gas so that the gas meets pipeline standards of $\leq 4$ ppm $H_2S$.

These and other objects are accomplished by a process in which a consortium of chemoautotrophic bacteria converts $H_2S$ and other sulfur species into elemental sulfur, which is recovered as a product. More particularly, the invention involves the use of the consortium under anaerobic conditions and at pressures of up to about 1000 psi and temperatures in the range of 50° F. to 140° F. (10° C. to 60° C.) to oxidize sulfur species such as $H_2S$ to elemental sulfur. In one embodiment of the invention, the process is carried out in a Pressure Reactor at pressures of about 1000 psi. The process of the invention is particularly suited for the removal of sulfide species from natural gas, although it may also be used to mitigate $H_2S$ in geothermal vent gas, enhanced oil recovery vent gas, off-gas streams in the chemical industry, landfill gas, and biogas. Other reaction conditions contemplated here are described below.

The present invention may be better understood by reference to the accompanying drawings in conjunction with the following description of the invention.

BRIEF DESCRIPTION OF THE DRAWINGS

FIG. 10 is a graph illustrating $H_2S$ conversion in the pressure reactor system of FIG. 3.

FIG. 11 is a graph illustrating the effect of temperature on the rate of removal of $CO_2$ in the pressure reactor system of FIG. 3.

Figure 1:
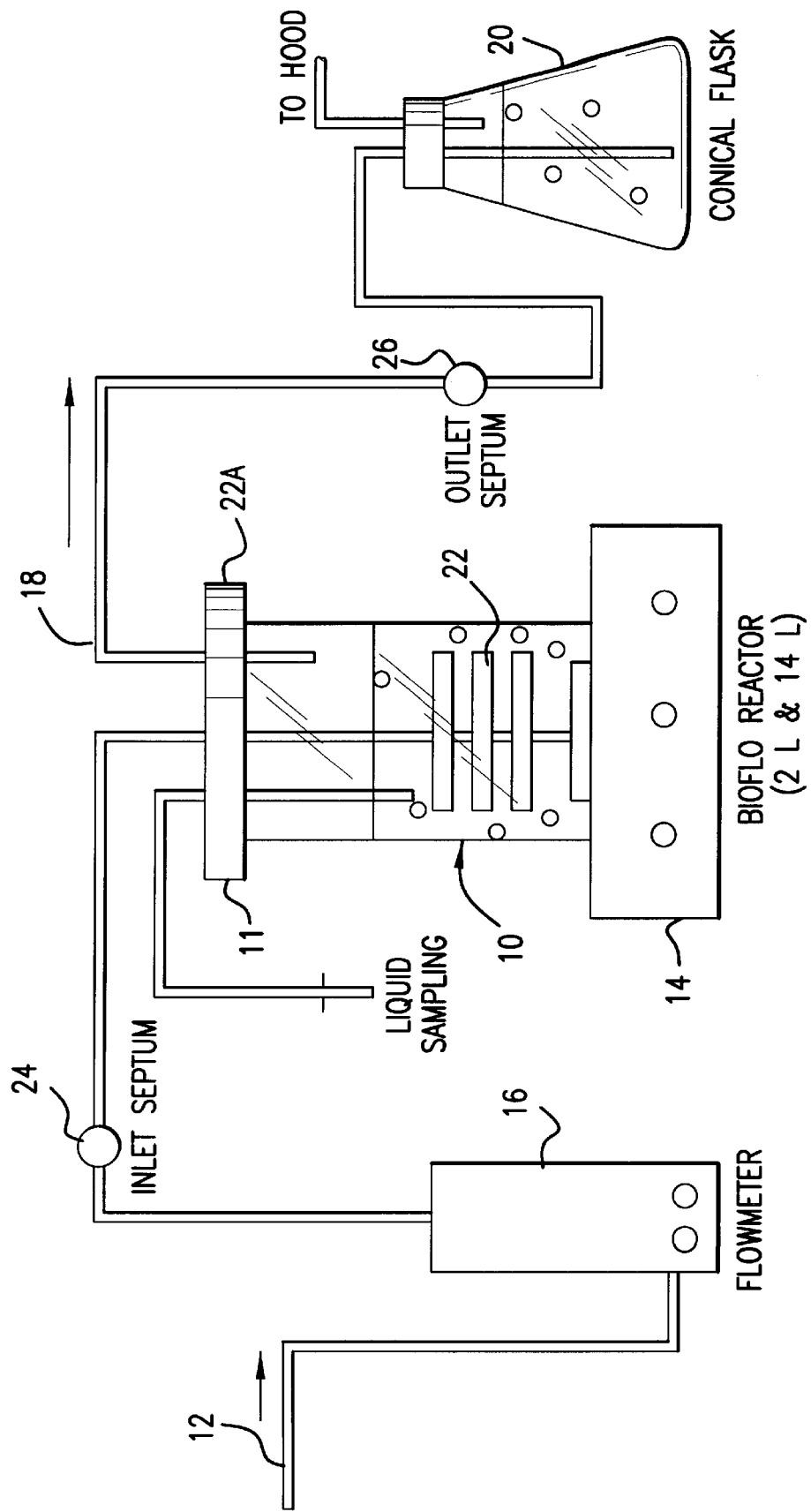
FIG. 1 is a flow diagram illustrating the process of the invention in a reactor at atmospheric pressure.

The microbiological consortium (hereinafter referred to as SSII) used in connection with the process of the present invention has been deposited in the American Type Culture Collection ATCC# (to be provided). This deposit was made by ARCTECH, Inc., on Oct. 6, 1998 with the ATCC Patent Depository and was acknowledged under the title, "Consortium SSII Sewage Sludge & Acid Mine Water Culture." Ms. Barbara M. Hailey of the ATCC informed Applicants that the ATCC Number for the deposit is ATCC 202177. The consortium comprises at least four morphologically distinct microbes.

The present invention may be carried out under any suitable conditions, the details of which can readily be ascertained by one skilled in this field in view of the present disclosure. Several non-limiting examples of suitable conditions follow.

Any suitable reactor can be used. Two examples are the reactors of FIGS. 1 and 3 as further described below.

The pressure of the sour gas stream can vary widely, without departing from the present invention. Atmospheric pressure and elevated pressures are specifically contemplated, though a sub-atmospheric pressure could also be used within the scope of the present invention. An elevated pressure from about 75 psi ($52 \text{ N/cm}^2$) to a pressure of or exceeding about 1000 psi ($700 \text{ N/cm}^2$) is specifically contemplated herein.

The reactor vessel may be maintained at any suitable temperature, for example, a temperature range of from about 50° F. to about 140° F. (10° C. to about 60° C.).

$H_2S$ can be present in the sour gas stream at any suitable concentration, for example, from a nominal concentration to about 10,000 ppm. Optionally, the concentration of $H_2S$ can be more than about 200 ppm, optionally more than about 5,000 ppm. The concentration can also vary within the scope of the invention.

The reactor vessel can contain from about 0.35% to about 10% biomass, or alternately at least about 5% biomass. Any suitable concentration of the biomass can be used, within the scope of the present invention.

The reactor vessel is desirably charged with an organic source of nitrogen. This may be done prior to pressurization or at other times, within the scope of the present invention.

The sour gas or other input gas stream which can be processed according to the present invention can contain hydrogen sulfide or other sulfur compounds. For example, any one or more of the following compounds may be present, and can be removed from the input gas stream by carrying out the present invention: $H_2S$, $CH_3SH$, $C_2H_5SH$, $(CH_3)_2S$, $CS_2$, or mixtures of any two or more of the foregoing species.

The input stream can also contain carbon dioxide, which the consortium according to the present invention can remove from the feed gas when the present invention is carried out under suitable conditions. For example, the input gas stream can contain from a nominal amount, alternatively at least about 5% by volume, to a larger amount, for example about 10% or more by volume, carbon dioxide. The consortium according to the present invention can, under suitable conditions, reduce the carbon dioxide content of the feed stream substantially, such as from a higher amount to less than about 2% by volume.

EXAMPLES

The following are several working examples illustrating how the present invention can be carried out. The scope of the invention is not limited in any way by the specific apparatus, conditions, and other details set out in the examples.

The SSII (ATCC—) used in connection with the present invention was cultivated in serum vials of 125 milliliter capacity under anaerobic conditions according to Srivastava, 1992. The serum vial contained 50 milliliters of the culture medium described in Table 1. The headspace of the vials was exchanged with an oxygen ($O_2$)-free mixture (80.20) of nitrogen ($N_2$), and carbon dioxide ($CO_2$). Vials were stoppered with butyl rubber stoppers and aluminum crimp sealed. The vials were then steam sterilized at 120° C. and 15 psi. Subsequently, the cooled vials were inoculated with 20% (w/o) of a previously cultivated culture of SSII. After 24 hours of cultivation at 68° F. (20° C.), the culture was inoculated in Wheaton bottles of 1 liter capacity containing 500 milliliters of culture medium (Table 1) and the bottles were prepared as described for the serum vials. The consortium was transferred into a maintenance medium having the composition set forth in Table 1. The SSII consortium and its medium were then used in the following experiments which illustrate the process of the present invention.

TABLE 1

Composition Of The Medium Component

| Medium Component | Quantity (g/L) |
| --- | --- |
| Disodium phosphate ($Na_2HPO_4$) | 1.20 |
| Potassium phosphate ($KH_2PO_4$) | 1.80 |
| Magnesium sulfate ($MgSO_4 \cdot 7 H_2O$) | 0.40 |
| Ammonium chloride ($NH_4Cl$) | 0.50 |
| Calcium chloride ($CaCl_2$) | 0.03 |
| Manganese sulfate ($MnSO_4 \cdot 7H_2O$) | 0.40 |
| Ferric chloride ($FeCl_3$) | 0.02 |
| Sodium bicarbonate ($NaHCO_3$) | 1.00 |
| Potassium nitrate ($KNO_3$) | 5.00 |
| Sodium thiosulfate ($Na_2S_2O_3$) | 10.00 |
| Trace metal solution | 15 mL |

TABLE 1-continued

Composition Of The Medium Component

|  | Quantity (g/L) |
|---|---|
| Trace Metal Solution Component | |
| EDTA | 5.0 |
| Zinc sulfate ($ZnSO_4$) | 2.2 |
| Calcium chloride ($CaCl_2$) | 0.554 |
| Manganese chloride ($McCl_2$) | 0.506 |
| Ferrous sulfate ($FeSO_4 7H_2O$) | 0.110 |
| Ammonium molybdate ($NH_4MoO_4$) | 0.157 |
| Cuprous sulfate ($CuSO_4$) | 0.157 |
| Cobalt Chloride ($CoCl_2$) | 0.161 |
| Water | 100 mL |

The experimental set-up for the following Experiments 1–4 is illustrated in FIG. 1. For each of these experiments, a liquid sample containing the SSII in its culture medium is loaded into a reactor 10, such as a BioFlo Reactor obtained from New Brunswick Scientific Co. The reactor 10 is then sealed with a stainless steel flange top 11. A simulated gas to be desulfurized is routed via line 12 into the reactor through a sparger 14 at the bottom of the reactor. A flowmeter 16, such as a Brooks flowmeter, is used to measure the flow rate of the simulated gas being passed into the reactor. The treated gas from the reactor is passed via line 18 through a sealed erlenmeyer flask 20 filled with water, with outlet connections to a fumehood (not shown). Bubbles in the flask downstream from the reactor indicate that the connections are leak proof. The reactor is also equipped with an agitator 22 in order to maintain the consortium in suspension. The gas concentrations of the synthetic gas entering and exiting the reactor 10 are determined from samples obtained via an inlet septum 24 and an outlet septum 26, respectively.

Experiment 1

One liter of the SSII in the culture medium described in Table 1 was transferred to a 2 liter capacity BioFlo reactor jar. Five milliliters of 10% Sheftone-T™, an organic nitrogen source obtained from Sheffields Products of Detroit, Mich., and 5 milliliters of 5% sodium thiosulfate were aseptically added to the reactor jar. The reactor vessel was then sealed with a stainless steel flange top. (See 11 of FIG. 1). The contents of the reactor were then stirred for 30 minutes.

A simulated sour natural gas (SNG) stream consisting of 5,000 ppm $H_2S$, 10.1% $CO_2$, 11.6% $N_2$ and 77.29% $CH_4$ was sparged at a rate of 1.2 liters per hour. The pH of the culture medium (Table 1) and the optical density (absorbance at 460 nm $OD_{460}$) of the liquid containing the SSII consortium were 7.5 and 0.63, respectively, at the start of the experiment. This optical density corresponded to a cell population of $10^6$ cells/mL. The inlet and outlet gas concentrations were measured as a function of time and are recorded in Table 2 below:

TABLE 2

| Time, (Hours) | Inlet $H_2S$ Concentration (ppm) | Outlet $H_2S$ Concentration (ppm) |
|---|---|---|
| 0 | 5905 | 0.65 |
| 1.0 | 5905 | 1.020 |
| 2.0 | 5454 | 3.16 |
| 3.0 | 5931 | 2.50 |

TABLE 2-continued

| Time, (Hours) | Inlet $H_2S$ Concentration (ppm) | Outlet $H_2S$ Concentration (ppm) |
|---|---|---|
| 4.0 | 5551 | 2.26 |
| 5.5 | 4620 | 1.014 |
| 6.0 | 5495 | 2.14 |
| 7.0 | 5781 | 2.91 |

The flow of the gas was stopped and the pH and $OD_{460}$ of the SSII suspension in the broth were 7.30 and 1.03, respectively. The SSII suspension was filtered with Whatman No. 1 filter paper to separate the larger suspended particles from the bacterial cells (SSII). Product analysis of the solid material indicated that the major product recovered was elemental sulfur. Then the liquid (filtrate) was centrifuged at 5,000 rpm×g to recover the cells of SSII from the liquid.

Experiment 2

A volume of 1.3 liters of the SSII in the culture medium of Table 1 was transferred to a 2 liter capacity BioFlo Reactor vessel. Similar to Experiment 1, a five milliliter suspension of 10% Sheftone-T™, and 5 milliliters of a 5% solution of sodium thiosulfate were added. The contents of the reactor vessel were agitated for one-half hour. A simulated sour natural gas stream containing 987 ppm of carbonyl sulfide (COS), 5029 ppm of $H_2S$, 996 ppm of methyl mercaptan ($CH_3SH$), 999 pm of ethyl mercaptan ($C_2H_5SH$), 1001 ppm of dimethyl sulfide (($CH_3)_2S$), 999 ppm of carbon disulfide ($CS_2$), 5% carbon dioxide ($CO_2$), 5% nitrogen ($N_2$) and the balance methane ($CH_4$) was sparged into the reactor at a rate of 1.2 L/h. The initial $OD_{460}$ and the pH of the SSII suspension were 1.57 and 8.12, respectively. The final $OD_{460}$ and pH at the end of the experiment were 3.3 and 6.74, respectively. Removal rates in terms of percentage removed were determined as a function of time and are recorded in Table 3 below:

TABLE 3

| Time, (Hours) | $H_2S$ % Removed | $CH_3SH$ % Removed | $C_2H_5SH$ % Removed | $(CH_3)_2S$ % Removed | $CS_2$ % Removed |
|---|---|---|---|---|---|
| 0 | 84.48 | 94.48 | 53.59 | 28.39 | 38.85 |
| 1 | 95.40 | 95.40 | 97.75 | 83.68 | 66.20 |
| 2 | 95.18 | 99.14 | 98.13 | 84.47 | 56.23 |
| 3 | 94.51 | 99.19 | 98.40 | 79.91 | 46.08 |

The results of this experiment demonstrate that the SSII can remove not only $H_2S$ from sour natural gas, but other sulfur species as well.

Experiment 3

Figure 2:
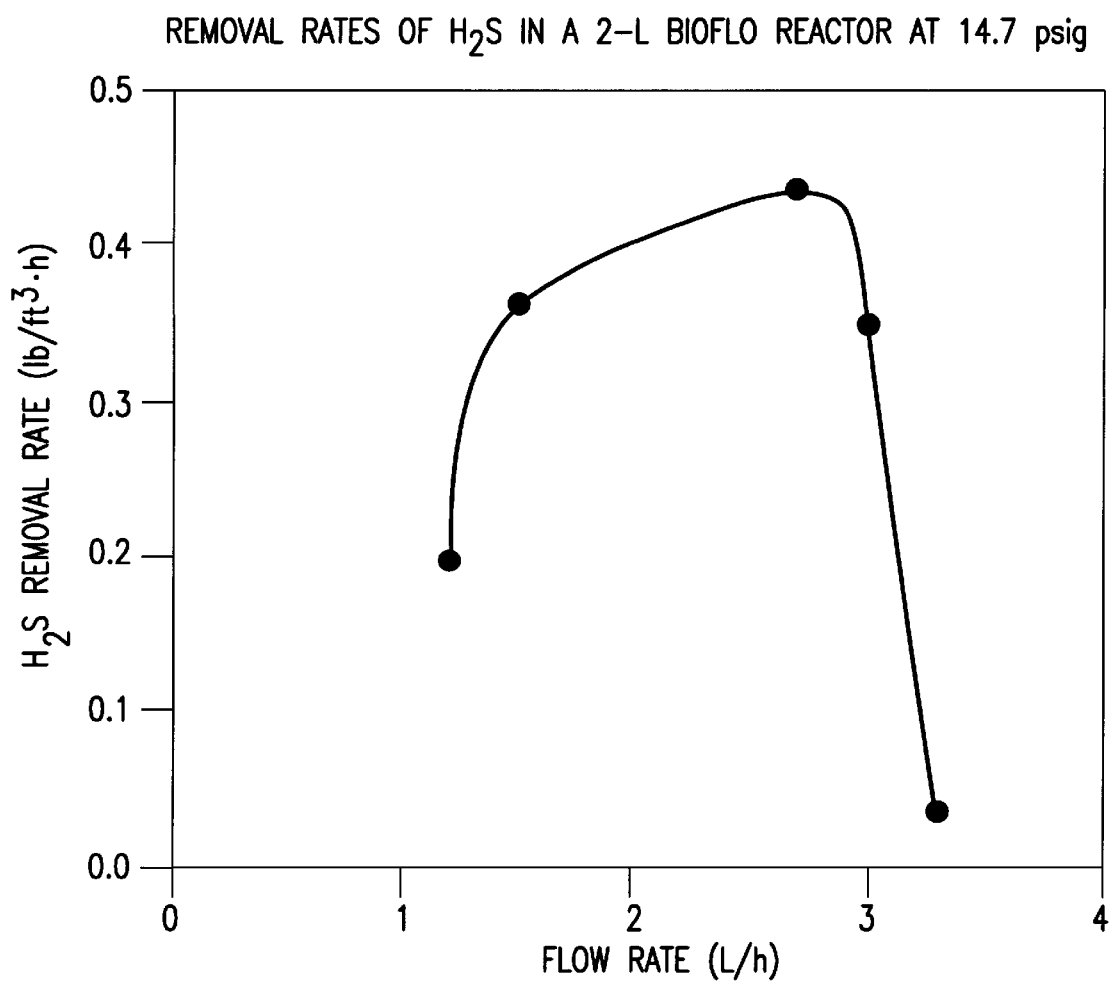
FIG. 2 is a graph illustrating $H_2S$ removal rates in the reactor of FIG. 1.

Experiment 1 was repeated except that the gas flow rate used in the process was varied. The specific oxidation rates in terms of sulfur removed as lbs/ft$^3$/hr were determined as a function of the gas flow rate and are shown in FIG. 2.

The results of this experiment demonstrate that the oxidation rate increases as the gas flow rate increases up to a limit of 2.7 L/h. Gas flow rates greater than 2.7 L/h resulted in a rapid decline of the specific oxidation rate. This is not a limitation of the SSII but of the reactor capacity. In order to test this hypothesis, experiment 4 was conducted.

Experiment 4

A volume of 12 liters of the SSII consortium in the culture medium of Table 1 was transferred to a 14 liter capacity reactor. A 100 milliliter volume of 8% SheftoneT™ and 30 milliliters of 20% Sodium and Potassium phosphates were added to the reactor. The contents of the reactor were stirred constantly. A simulated natural gas stream containing $H_2S$ was sparged into the reactor at 8.64 L/h. The gas composition was 5% carbon dioxide, 5% nitrogen, 1% hydrogen sulfide, and the balance methane. The initial pH and $OD_{460}$ were 7.4 and 2.70, respectively. The inlet and outlet gas concentrations were measured as a function of time and are recorded in Table 4 below:

TABLE 4

| Time, (Hours) | Inlet $H_2S$ Concentration (ppm) | Outlet $H_2S$ Concentration (ppm) |
|---|---|---|
| 0 | 3207 | 0 |
| 1 | 3217 | 0 |
| 3 | 3060 | 0 |
| 4 | 3286 | 0 |
| 5 | 3281 | 0 |
| 6 | 3290 | 0 |
| 7 | 3288 | 0 |

Thus, the experiment showed that the hypothesis is correct.

Figure 3:
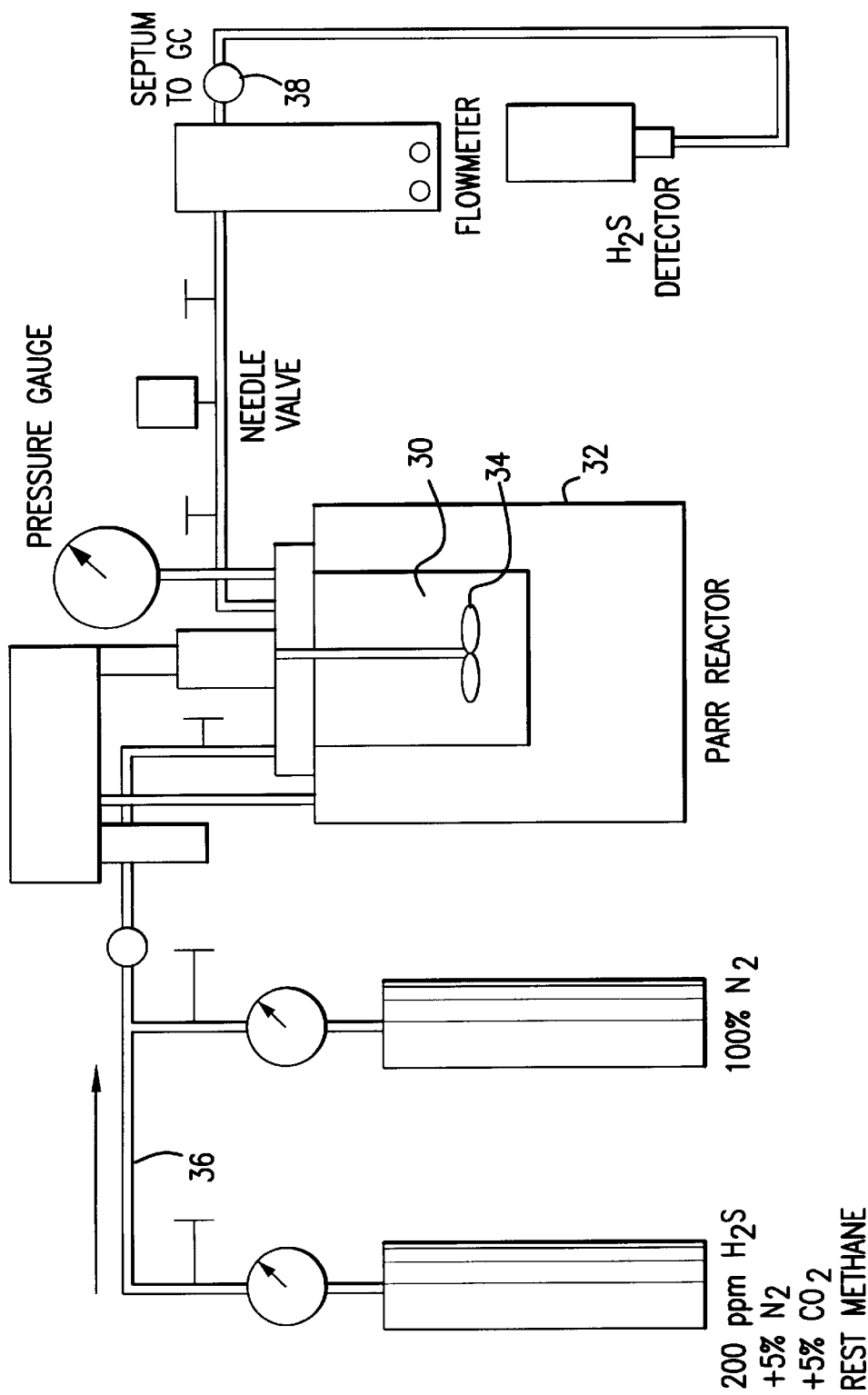
FIG. 3 is a flow diagram of the pressure reactor used in a preferred embodiment of the invention.

The experimental set-up for the following Experiments 5–8 and 10–12 is illustrated in FIG. 3.

For these experiments, a liquid sample containing the SSII consortium in its culture medium is loaded into a pressure reactor 30, such as a Parr pressure reactor. The pressure reactor is made of stainless steel and is housed in a metallic shell 32. The reactor can be pressurized up to 2000 psi. An agitator 34 is provided inside the reactor to maintain the SSII consortium in suspension. A simulated sour natural gas to be desulfurized is introduced into the reactor via inlet line 36. Periodic gas samples from the head space of the reactor are withdrawn through a septum 38 so that progress of the desulfurization process can be monitored.

Experiment 5

Six hundred milliliters of SSII in the culture medium of Table 1 are charged into the pressure reactor after adding 10 milliliters each of 5% Sheftone-T™ and 5% sodium thiosulfate. The initial pH and $OD_{460}$ of the culture broth are 8.16 and 1.66, respectively. The reactor is pressurized to 1000 psi with a sour gas stream containing 5000 ppm $H_2S$. The agitator is started, and the gas concentration in the head space is monitored at particular intervals of time by withdrawing gas samples through the septum. The readings are noted as a function of time and are recorded in Table 5 below:

TABLE 5

| Time (Hours) | $H_2S$ Concentration (ppm) |
|---|---|
| 0 | 1744 |
| 1 | 1680 |
| 3 | 1609 |
| 5 | 1566 |
| 20 | 1146 |
| 23 | 921 |
| 25 | 442 |
| 26.5 | 191 |
| 26.75 | 0.25 |

When the $H_2S$ is mitigated, the pressure is released and the pH and optical density of the liquid sample are measured. The liquid sample has a pH of 6.40 and an optical density of 3.26. The results of this experiment demonstrate that the SSII consortium can remove $H_2S$ to meet regulatory pipeline standards even at a pressure of 1000 psi in a semi-continuous mode.

Experiment 6

The process of Experiment 5 was repeated, except that different pressures, ranging from 75 psi to 1000 psi, were selected for the reactor, taking into consideration the compressibility factor. The rates of removal of $H_2S$ by the SSII consortium obtained at the different pressures are tabulated below in Table 6.

TABLE 6

| Rates Of Removal Of $H_2S$ At Different Pressures | |
|---|---|
| Pressure, psi | $H_2S$ removal rate, mmols/h |
| 75 | 0.191 |
| 100 | 0.126 |
| 200 | 0.112 |
| 500 | 0.109 |
| 700 | 0.205 |
| 800 | 0.210 |
| 1000 | 0.325 |

The data demonstrate that at a higher pressure of 7500 psi, there is a direct relationship between pressure and the faster removal rate of $H_2S$, i.e. the higher the pressure, the higher is the removal of $H_2S$.

Experiment 7

Figure 4:
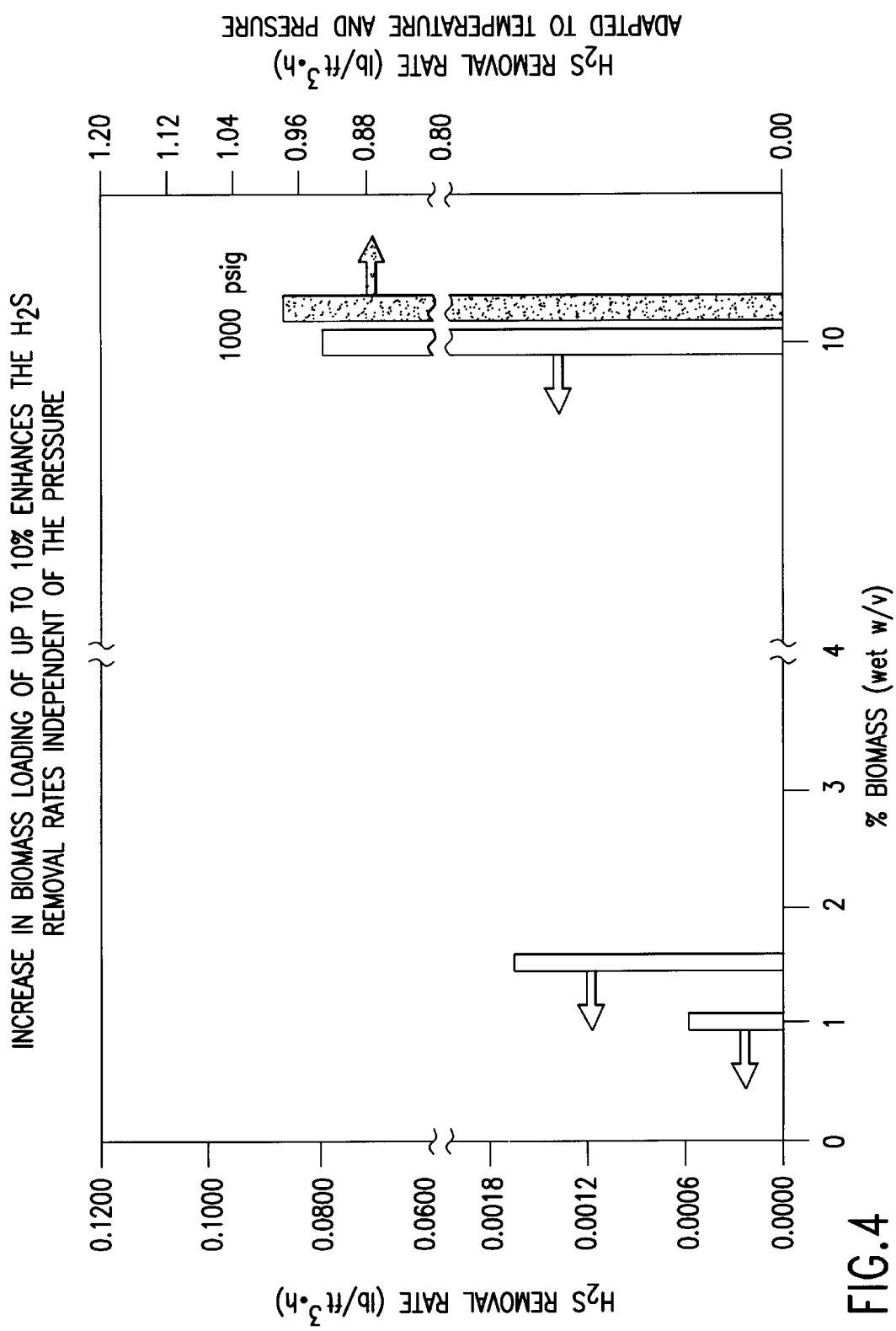
FIGS. 4 and 5 are graphs illustrating the effect of cell density on $H_2S$ removal rates.
Figure 5:
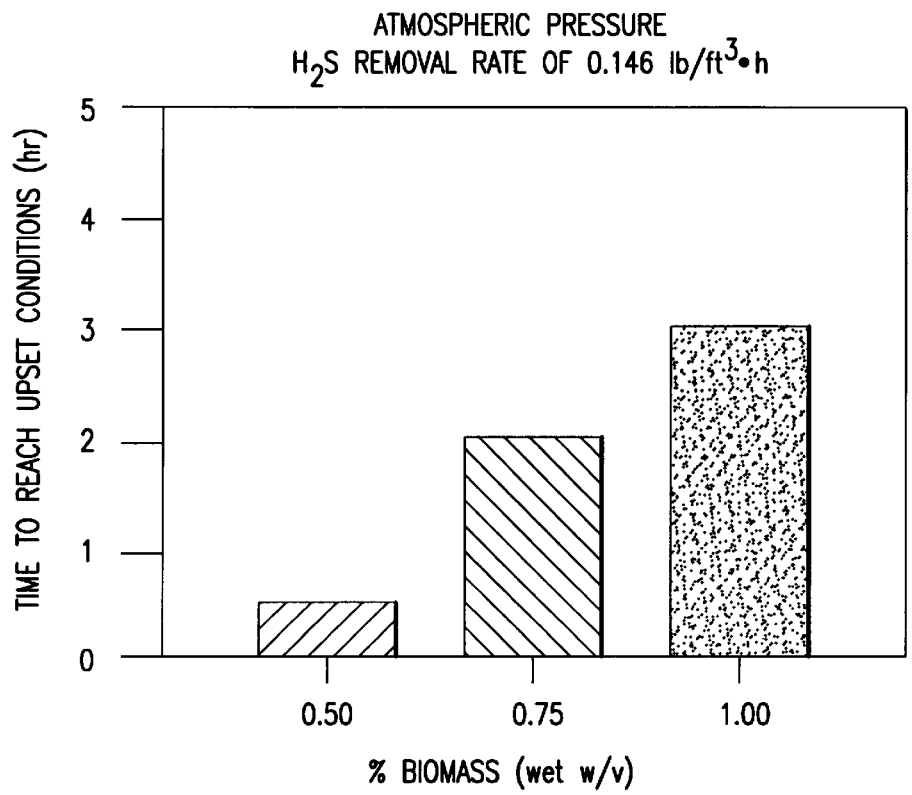

The process of Experiment 5 was repeated except that in this experiment, the cell mass (wet weight of cells/600 ml of the culture medium) was varied in the range of 0.35% to 10%. In each of these runs, the initial pH of the culture medium was 7.5, and the pressure was 1,000 psi. The rates of $H_2S$ removal under these conditions are graphically presented in FIGS. 4 and 5. This data indicates that the higher the cell density, the higher the removal rate of $H_2S$.

Experiment 8

Figure 6:
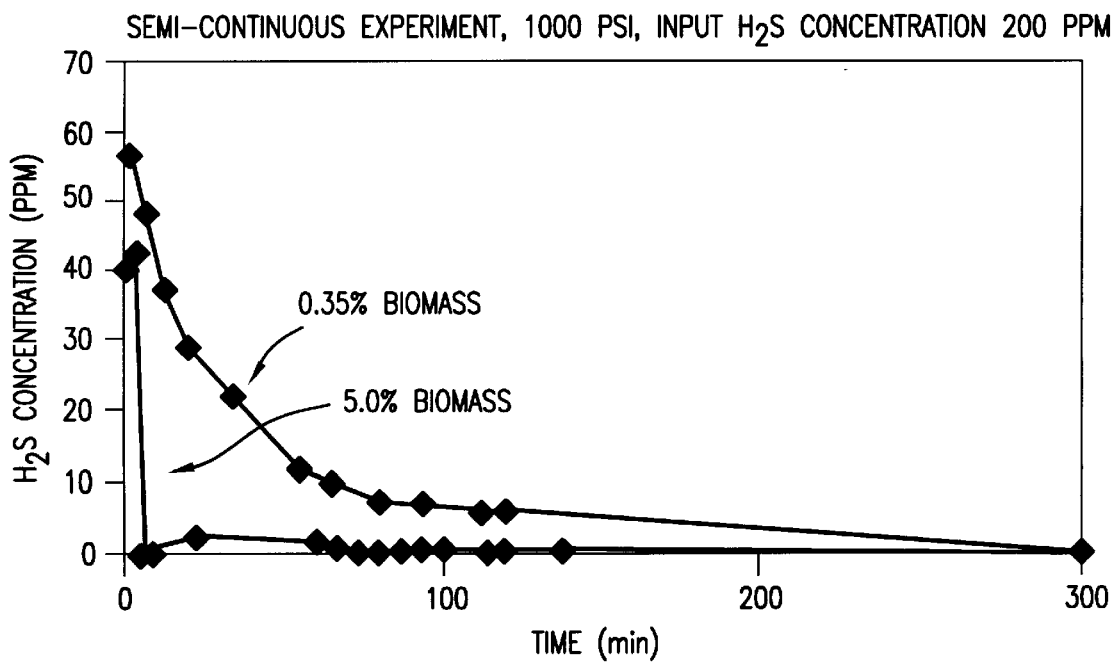
FIG. 6 is a graph illustrating the effect of biomass amount on the amount of time required to oxidize $H_2S$.

The process of Experiment 7 was repeated, except that in this experiment, the cell masses of 0.35% and 5% were compared at an initial $H_2S$ concentration of 200 ppm in a semi-continuous mode, and the gas inlet flow 10 times higher than the previously determined ratio of 1:1.6 between the reactor working volume verses the gas flow rate per hour, which for a 600 milliliter culture volume will be 0.96 liters per hour. Thus, the inlet flow rate of sour natural gas in this experiment was 9.6L/h. The data on outlet $H_2S$ concentration is presented in FIG. 6. This data indicates that the contact time is reduced by two orders of magnitude (300 to 3 mins.) at 10 times the flow rate.

Experiment 9

Figure 7:
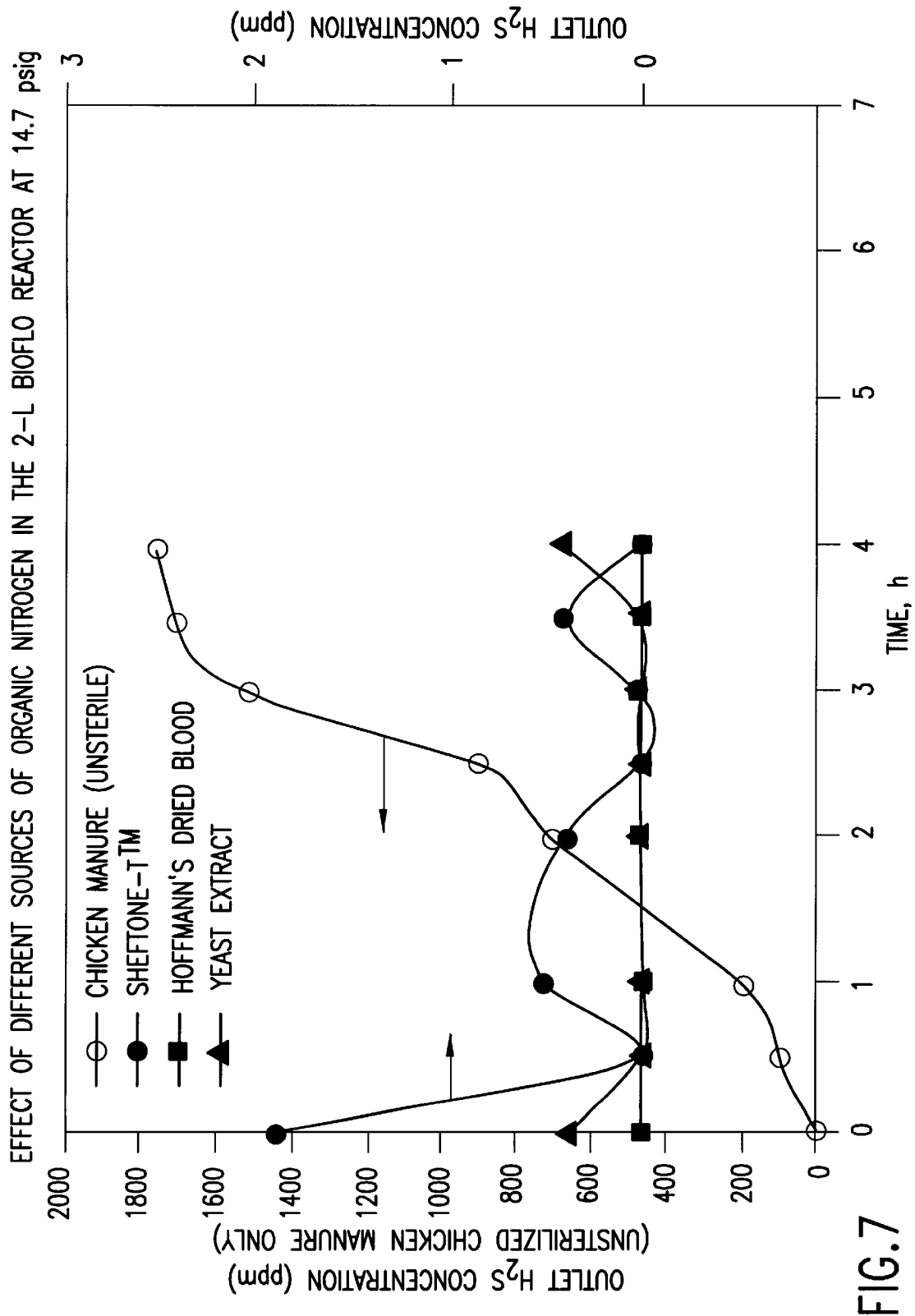
FIGS. 7 and 8 are graphs illustrating the effect of different nitrogen sources in the reactor of FIG. 1.
Figure 8:
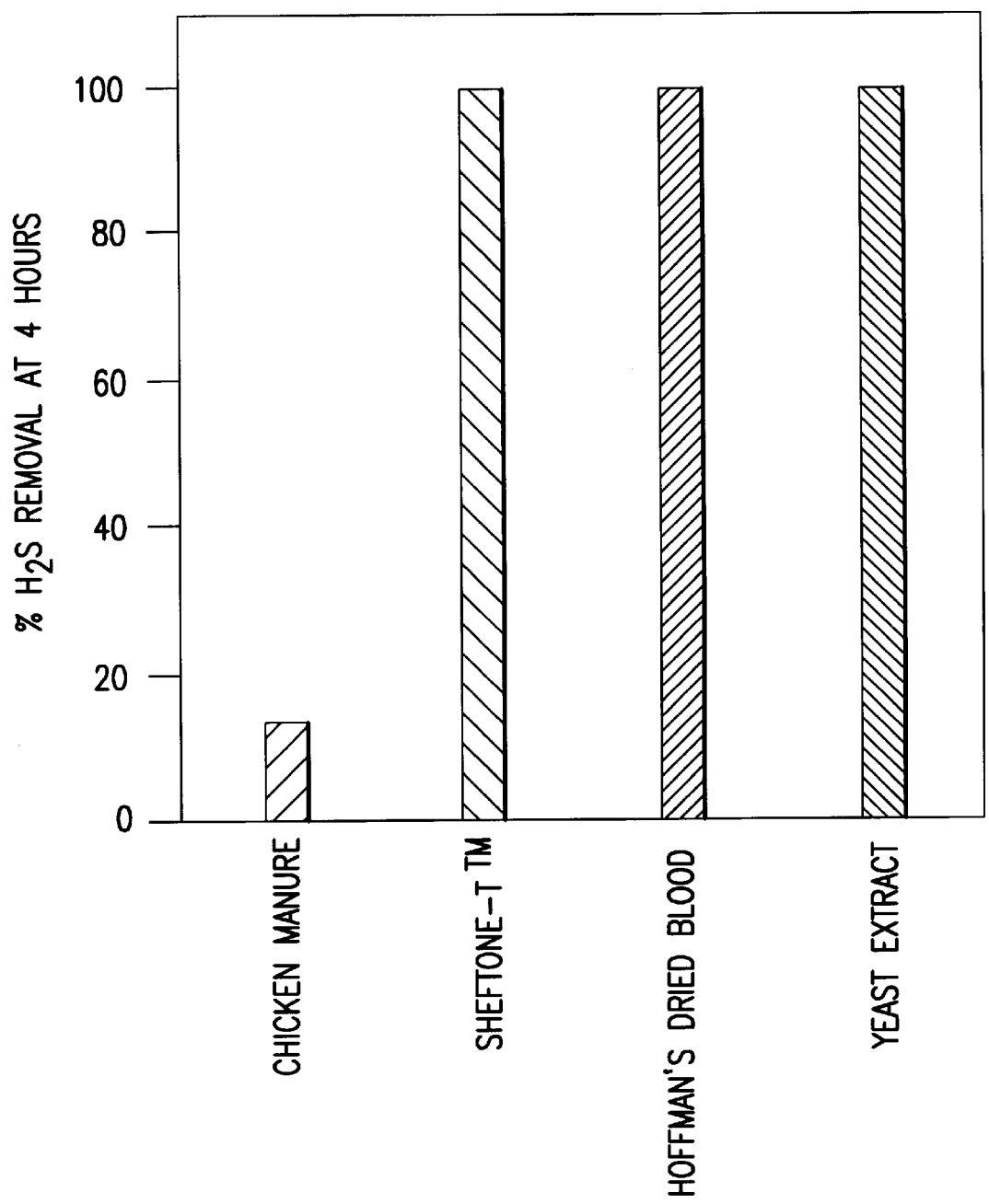

The process of Experiment 1 was repeated, using the reactor illustrated in FIG. 1, except that alternative sources of organic nitrogen were substituted for the Sheftone-T™ suspension. The alternative sources of nitrogen used were Hoffman's dried blood (a commercially available source of organic nitrogen), Cargill 200/20 (an organic source of nitrogen available from Cargill Corp.), and different lots of chicken manure collected at different times from a local poultry farm. Each alternative nitrogen source was added in an amount to give the same organic nitrogen equivalent as provided by adding 5 milliliters of 10% Sheftone-T™ suspension. In each of these runs, the initial pH of the culture medium was 7.5 and the cell concentration was 10% (wet weight of cells/1000 ml of culture broth). The initial $H_2S$ concentration was 10,000 ppm. The rates of removal of $H_2S$ under these conditions, or conversely the remaining $H_2S$ in the outlet gas are graphically illustrated in FIGS. 7 and 8. The data indicates that the highest and most consistent $H_2S$ removal was obtained when Cargill 200/20 was the source of organic nitrogen. This is also the most economical organic nitrogen source with a consistent nitrogen content.

In addition to the alternative organic nitrogen sources utilized in this example, other organic nitrogen sources, such as solubilized sewage sludge, and deactivated animal and/or poultry manure, could also be utilized.

Experiment 10

Figure 9:
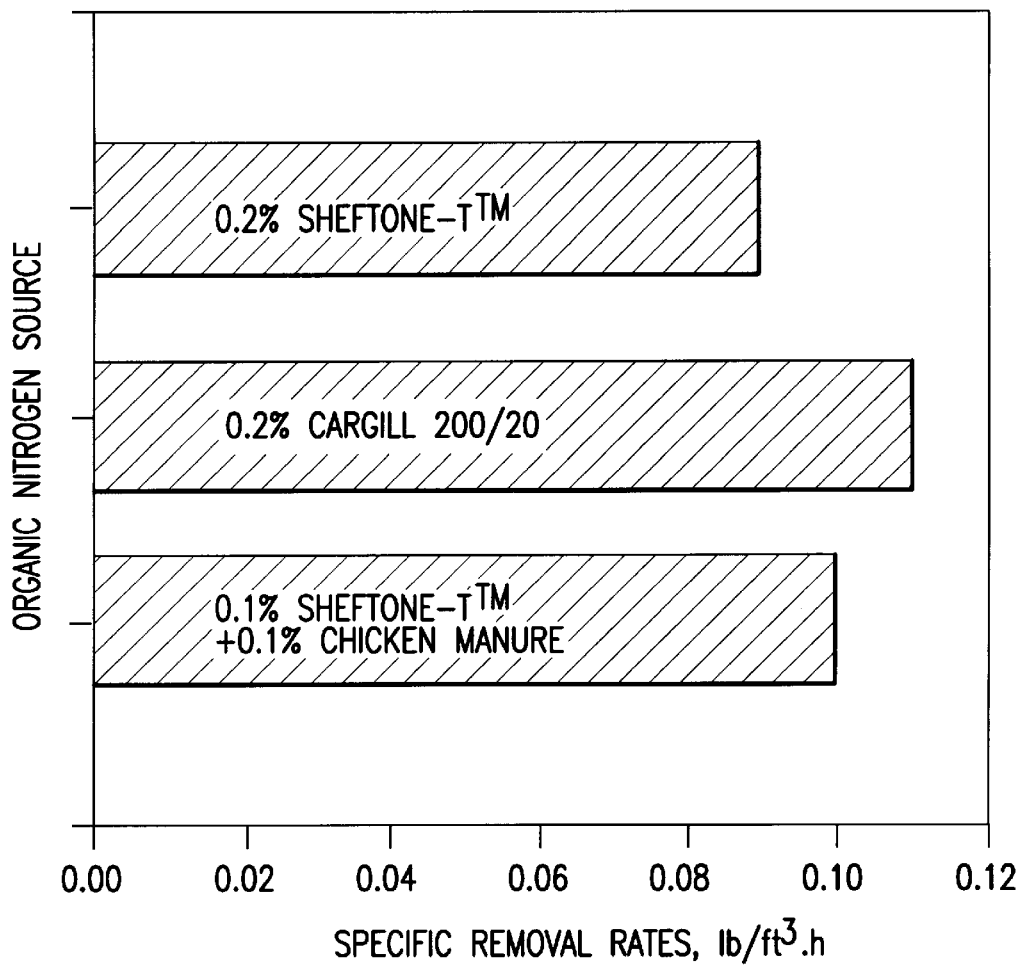
FIG. 9 is a graph illustrating the effect of different nitrogen sources in the reactor of FIG. 3.

The process of Experiment 9 was repeated except that the process was carried out in the pressure reactor system of FIG. 3 and the organic sources of nitrogen were Cargill 200/20 and a combination of Sheftone-T™ and chicken manure. Each alternative nitrogen source was added in an amount to give the same organic nitrogen equivalent as provided by adding 5 milliliters of 10% Sheftone-T™ suspension. In each of the runs, the initial pH of the culture medium was 7.5 and the cell concentration was 10% (wet weight of cells/600 ml of culture broth). The initial $H_2S$ concentration was 10,000 ppm. The rates of removal of $H_2S$ under these conditions are illustrated in FIG. 9. The data indicates that, although each of the organic nitrogen sources are effective in the desulfurization process, the highest rate of $H_2S$ removal was again obtained when Cargill 200/20 was the source of organic nitrogen.

Experiment 11

The process of Experiment 5 was repeated, except that the process was conducted at different temperatures ranging from 50° F. (10° C.) to 140° F. (60° C.) and the initial $H_2S$ concentration in the gas was 10,000 ppm. The rates of removal of $H_2S$ by the SSII consortium obtained at the different temperatures, while maintaining a pressure of 1000 psi, are graphically illustrated in FIG. 10. As FIG. 10 shows, higher rates of removal of $H_2S$ are achieved at both elevated temperatures and pressures.

Experiment 12

The process of Experiment 11 was repeated, except that removal of $CO_2$ was monitored rather than removal of $H_2S$. The inlet sour natural gas contained 10.1% $CO_2$. Sixty gram wet weight SSII (10%) was suspended in 600 milliliters of medium, described in Table 1, containing 0.2% (weight/volume of medium) Cargill 200/20. The data is presented in FIG. 11. This data shows that the removal rates of $CO_2$ remains about the same up to a temperature of 104° F., but increases thereafter and at 140° F. is 0.616 $lb/ft^3$ per hour.

We claim:

1. A process for the anaerobic removal of sulfur containing compounds from a gas stream comprising the steps of:

charging a reactor vessel with a microbial consortium of chemoautotrophic bacteria;

maintaining the reactor vessel at a temperature range of between about 77 degrees F. and about 140 degrees F.;

pressurizing said reactor with a malodorous gas stream containing the sulfur containing compounds to a pressure of between about 75 psi to about 1000 psi wherein sulfide in the gas stream is oxidized to elemental sulfur by the microbial consortium.

2. A process according to claim 1, wherein the reactor vessel is maintained at a temperature range of between about 100° F. and about 140° F.

3. A process according to claim 1, wherein the concentration of hydrogen sulfide in the gas stream containing the sulfur containing compounds is up to about 10,000 ppm.

4. A process according to claim 1, wherein the microbial consortium of chemoautotrophic bacteria charged into the reactor vessel has a wet cell mass of from about 0.35% to about 10.0% biomass.

5. The process according to claim 1, wherein an organic source of nitrogen is charged into the reactor prior or pressurization.

6. The process according to claim 1, wherein the gas stream includes at least one sulfide from the group consisting of hydrogen sulfide, methyl mercaptan, ethyl mercaptan, dimethyl mercaptan, carbon disulfide, and mixtures thereof.

* * * * *